United States Patent [19]

Nasrallah et al.

[11] Patent Number: 5,859,328
[45] Date of Patent: Jan. 12, 1999

[54] ISOLATED DNA ELEMENTS THAT DIRECT PISTIL-SPECIFIC AND ANTHER-SPECIFIC GENE EXPRESSION AND METHODS OF USING SAME

[75] Inventors: Mikhail E. Nasrallah; June B. Nasrallah, both of Ithaca, N.Y.; Mary K. Thorsness, Laramie, Wyo.

[73] Assignee: Cornell Research Foundation, Inc., Ithaca, N.Y.

[21] Appl. No.: 485,158

[22] Filed: Jun. 7, 1995

Related U.S. Application Data

[63] Continuation of Ser. No. 54,362, May 3, 1993, abandoned.
[51] Int. Cl.$^6$ .......................... C12N 15/29; C12N 15/82; A01H 4/00; A01H 5/00
[52] U.S. Cl. .................... 800/205; 536/24.1; 435/69.1; 435/70.1; 435/240.4; 435/172.3; 435/320.1
[58] Field of Search ................. 536/24.1; 435/172.3, 435/320.1, 240.4, 69.1, 70.1; 800/205

[56] References Cited

U.S. PATENT DOCUMENTS

| | | | |
|---|---|---|---|
| 5,023,179 | 6/1991 | Lam et al. | 435/172.3 |
| 5,053,331 | 10/1991 | Clarke et al. | 435/172.3 |
| 5,097,025 | 3/1992 | Benfey et al. | 536/27 |
| 5,110,732 | 5/1992 | Benfey et al. | 435/172.3 |

FOREIGN PATENT DOCUMENTS 0 412 006 A1  2/1991  European Pat. Off.

OTHER PUBLICATIONS

Dzelzkalns et al 1993 (Aug.) The Plant Cell 5:855–863.
Thorsness et al 1991 Devel. Biol. 143:173–184.
Toriyama et al 1991 Devel. Biol. 143:427–431.
Sato et al 1991 The Plant Cell 3:867–876.
Murfett et al 1992 (Sep.) The Plant Cell 4:1063–1074.
Budelier et al 1990 Mol. Gen. Genet. 224:183–192.

*Primary Examiner*—Douglas W. Robinson
*Assistant Examiner*—Thomas Haas
*Attorney, Agent, or Firm*—Sughrue, Mion, Zinn, Macpeak & Seas, PLLC

[57] ABSTRACT

Isolated DNA elements that direct either pistil-specific or anther-specific expression of a polypeptide-encoding gene are disclosed. Plants comprising the DNA fragment operably linked to a gene are also disclosed. A further embodiment comprises a method of producing a female sterile plant, the method comprising growing a plant having integrated into its genome an isolated DNA element that directs pistil-specific expression of a nucleotide sequence that encodes or is transcribed into a moiety that causes female sterility in plants.

21 Claims, 6 Drawing Sheets

FIG. 3(A)

```
S13   -289 ATTTTCTAACAGACTTAGATGCACTTGCTGAACACATACTTGCTGAACACCATATGTTATG
S2    -311 ACTTGAATGTATCGAATCATACTATTGAGACCACCATACTTGCGAATACCATATGCTATG
S8
SLR1  -356 TTTTAAGTCAAACTGAAGGAAACAACATATGATATGTTATGTCATTGGTCCAAAACACA
```

```
                                                            Box I
S13   -228 TTGGCAGGGTGAGAAATTAATCACGTGTAGATATAGAAGTAGTA | GAC AAATGATA TAG
S2    -250 TTGACAGCGTGAG AACTAATAACGTGTAGATATAAAAGTAGTT | GACTGAATGATA CAA
S8    -202                           GTAGTAGGTATAAAGTAGTG | GAC AAATGATA CAC
SLR1  -295 ATGTTACGTTGCATGAGAAATCAATTTCACGTGGTAAGGTTACT | GAC CAATGACA ATA
```

```
           Box II                  Box III                              Box IV
S13   -170 GTTTGT GGGAA TGAATTAATCG ATGGGA | TGAAAAAGTCATCGA ACATGTAACACCA
S2    -192 GTTTGT GGAAG TGACTTAATCG TAGGGA | TGAAAAAGTCATGGA CTATGGAACACAA
S8    -167 GTTTTT GGAAA TGAATTAATCG ATGGGA | TGAAAAAGTCATCGA ACATGTAACACCA
SLR1  -237 GTTTGT TAAAA TGAGTTAAT G AGTGGC | TGG AAAGTCATAGA ATGTGGAAATAAA
```

FIG. 3(B)

```
           Box V
S13   -114 C ATTTTACTTGTCTGCT AGGTTCGTGATAGTCGTTAAATTAGATACGTGAAAAAGAT
S2    -136 C ATTTTGCTTGCCAGTT AGGTTCGTCATAATAGTTTAA TTCGAATTTTCTTGCAAAGT
S8    -111 C ATTTTGCTTGTCTGCT AGGTTCCTTATAGTCGTTTAAAATCTGTATGTGG AAAAGAT
SLR1  -183 A AATTTTCTTGTCTGCT GGAAAGTATATATATCTACAATTAAGACATAAACCATGCAA

S13   - 55 TATAAATATGCAAAGGGGAAGAAAGAAAGAAAGGAGGGGAGAGAA
S2    - 78 AACTTAGGATGTATATATGTGCAAGTAGGACAAAACTAACACAAGAAAAAAGAA
S8    - 53 TATAAATAAGCAA GGGGAGGGGAAAGAAAGAACAAGGTGGGGAGAGAA
SLR1  -124 ATTAAAATCAAACCATCCTCATTAGGTTTGCAAATCTAATAAAGACATAAAGTCCATATGT

S13
S2    - 17 AGAAAGTGGTGGGAAA
S8
SLR1  - 63 AACAATTTTTTCTATAAAATAACGGGCGACAATGCATAGAAAATTAAAGTGGTGAAGAGAGAG
```

FIG. 4

```
-475  TGCTGAGATG  GATTTACAAT  TTGATTTCTT  TTGTATTTTT  ATTTGGTGTG  TTTAATATAT
-415  TAGTTAACCA  ATTACGTTA   TACCAAATTT  TTCAACCCTC  TTTTTAGTAA  AAAACGAAAT
-355  TAAAGTTTTT  TCCCTCTTAG  TCCGACGATT  TTAAGCTAAT  TAGTTCGAAC  AAAGAGTACA
-295  ACATTA
```

ISOLATED DNA ELEMENTS THAT DIRECT PISTIL-SPECIFIC AND ANTHER-SPECIFIC GENE EXPRESSION AND METHODS OF USING SAME

This is a Continuation of application Ser. No. 08/054,362 filed May 3, 1993 (abandoned).

The making of this invention was supported in part by funds from the United States Government. Therefor the United States Government might have certain rights to this invention.

FIELD OF THE INVENTION

The present invention relates to directing pistil- and anther-specific gene expression in transformed plants. In particular, the present inventors have established the minimal sequence elements of the S-locus glycoprotein (SLG) gene promoter necessary for this expression pattern.

BACKGROUND OF THE INVENTION

Self-incompatibility, a mechanism that prevents self-fertilization in flowering plants, is based on the ability of the pistil to recognize the presence of self-pollen and on the female tissue's capacity to restrict the growth or germination of self-related but not of genetically unrelated pollen. Although the mechanism of self-recognition is not yet known, a chromosomal location, the S-locus, has been shown from genetic crosses to encode the putative pistil and pollen elements that interact in this recognition process. When both the captured pollen grain and the receptive pistil possess and express different S-locus haplotypes, pollen growth proceeds; when the two S haplotypes are identical, pollen growth, as well as self-pollination, are prevented. The expression of S-locus encoded elements in two tissues, the female sporophytic tissue as well as in the anther or pollen (or in both male tissues), is a hallmark of all models of self-incompatibility and distinguishes gene regulation in this system from many other systems in which tissue specificity is limited to a single location.

Self-incompatibility has been best studied in the Brassicaceae and Solanaceae, and genes associated with the S-locus have been identified in species of Brassica, Nicotiana, Petunia, and Solanum. In Brassica, two partially homologous genes have been shown to reside at the S-locus: one, SLG, encodes a secreted glycoprotein that is present in stigma papillar cells and in the tapetum and microspores of the anther, and the other, SRK, specifies a putative membrane-spanning receptor protein kinase that is present in Brassica pistil and anther. Expression of the S-locus products in the Brassicas is controlled sporophytically. A haploid pollen grain will possess a self- incompatibility phenotype that is determined by the two S-locus alleles carried by the parent plant. In contrast, the self-incompatibility phenotype of pollen derived from plants that express gametophytic control of self-incompatibility (e.g., in the Solanaceae) is dictated by the single S-locus haplotype carried by the pollen.

Evidence for this specificity of SLG promoter activity derives from genetic ablation studies in which a chimeric gene construct consisting of the SLG promoter fused to the diphtheria toxin subunit A (DTA) gene was introduced into tobacco (M. K. Thorsness, M. K. Kandasamy, M. E. Nasrallah and J. B. Nasrallah, Dev. Biol., Vol. 143, (1991) pages 173–184), Brassica (M. K. Kandasamy, M. K. Thorsness, S. J. Rundle, J. B. Nasrallah and M. E. Nasrallah, Plant Cell, Vol. 5, (1993) (in press)), and Arabidopsis (M. K. Thorsness, M. K. Kandasamy, M. E. Nasrallah and J. B. Nasrallah, Plant Cell, Vol. 5, (1993) (in press)). Transformation of these plants with the SLG-DTA gene fusion resulted in the production at high frequency of transgenic plants that underwent normal differentiation and produced flowers in which only specific cells of the pistil and anther were ablated.

Surprisingly, when the Brassica SLG gene is introduced into Nicotiana tabacum, a self-compatible species belonging to the Solanaceae family, it is expressed in pistils in a manner similar to that noted for the S-linked RNase of Nicotiana alata and not according to the pattern shown for this gene in Brassica. In transgenic tobacco, the product of the introduced Brassica SLG gene accumulates in the secretory zone of the stigma, the transmitting tissue of the style, and to a lesser degree in the placental epidermis of the ovary. In Brassica, endogenous SLG molecules are detected mainly in the cell wall of stigma papillar cells. These expression patterns are consistent with the site and timing of self-pollen rejection in Brassica and Nicotiana.

Similar findings have been made with regard to S-locus expression in the anther. The analysis of the SLG-DTA fusion and of a reporter gene fusion consisting of the SLG promoter fused to the reporter β-glucuronidase (GUS) gene have identified the cell types of the pistil and anther in which the SLG promoter is active. In the pistils of transgenic Brassica and Nicotiana, the promoter is active in cells of the stigma and in the transmitting tissue of the style and ovary (T. Sato, M. K. Thorsness, M. K. Kandasamy, T. Nishio, M. Hirai, J. B. Nasrallah and M. E. Nasrallah, Plant Cell, Vol. 3, (1991) pages 867–876; M. K. Thorsness, M. K. Kandasamy, I. E. Nasrallah and J. B. Nasrallah, Dev. Biol., Vol. 143, (1991) pages 173–184). In the anthers of transgenic Brassica, promoter activity is evident in the tapetum, a sporophytic tissue of the anther, and in microspores (T. Sato, M. K. Thorsness, M. K. Kandasamy, T. Nishio, M. Hirai, J. B. Nasrallah and M. E. Nasrallah, Plant Cell, Vol. 3, (1991) pages 867–876). In transgenic tobacco anthers on the other hand, the SLG-GUS fusion exhibits strict gametophytic expression: GUS activity is detected in pollen grains and not in the sporophytic tissues of the anther (M. K. Thorsness, M. K. Kandasamy, M. E. Nasrallah and J. B. Nasrallah, Dev. Biol., Vol. 143, (1991) pages 173–184). Moreover, approximately one half of the pollen grains of transformed plants that contain a single copy of the introduced gene show GUS activity. On the other hand, Brassica plants transformed with this construction display GUS activity in the tapetum, a sporophytic tissue of the anther, and in pollen microspores. Thus, although the S-locus-linked genes identified to date differ in plants possessing sporophytic and gametophytic forms of self-incompatibility, a common, conserved mechanism apparently exists in Brassica and Nicotiana for directing the expression of S-locus genes.

The DNA sequences required in cis for the expression of the SLG gene lie within 3.65 kb upstream of the gene's coding region. Promoter activity is detected in both pollen and pistil of transformed Brassica and Nicotiana plants and follows the temporal, spatial, and developmental-regulated expression pattern noted above.

SUMMARY OF THE INVENTION

Accordingly, one object of the present invention is to demonstrate that there are distinct cis-acting elements that direct pistil-specific and anther-specific activity and to define these elements.

Another object of the present invention is to define the uses of the elements to produce plants that express a specified gene in only the pistil or anther.

The present invention is drawn to isolated DNA elements which are capable of directing pistil-specific expression of a nucleotide sequence, when the sequence is operably linked to a minimal promoter. In this manner, minimal promoters can be utilized in combination with the DNA elements of the invention to direct pistil-specific expression of a nucleotide sequence of interest.

DNA elements are also provided which are capable of directing anther-specific expression.

The DNA elements of the invention can be utilized in combination with promoters, preferably minimal promoters, and nucleotide sequences, including sequences encoding polypeptides of interest and anti-sense RNA.

The present invention further provides methods of selectively expressing a gene in plant pistils or plant anthers, the methods comprising growing a plant having integrated into its genome the above-described isolated DNA elements, or functional equivalents of the isolated DNA elements, operably linked to a nucleotide sequence that is operably linked to a promoter.

In a preferred embodiment, the method produces a female sterile plant or a male sterile plant by operably linking the DNA element that directs pistil-specific expression or anther-specific expression, respectively, to, e.g., a gene that encodes a moiety that is cytotoxic to plant cells.

BRIEF DESCRIPTION OF THE DRAWINGS

FIG. 3(A) (SEQ ID NOS:6–9) shows the nucleotide sequence and alignment of portions of the promoter regions of the $SLG_{13}$, $SLG_2$, $SLG_8$, and SLR1 genes. The boxes outline five regions that show particular conservation among the four sequences. The sequences are numbered from the translation initiation codon of each gene. FIG. 3(B) nucleotides 1–186 of SEQ ID NO:6 shows the nucleotide sequence of a portion of the promoter region of the $SLG_{13}$ genes 5' adjacent to the portion shown in FIG. 3(A).

FIG. 4 is a diagrammatic representation of the arrangement of functional elements within the $SLG_{13}$ promoter.

DETAILED DESCRIPTION OF THE INVENTION

Figure 1:
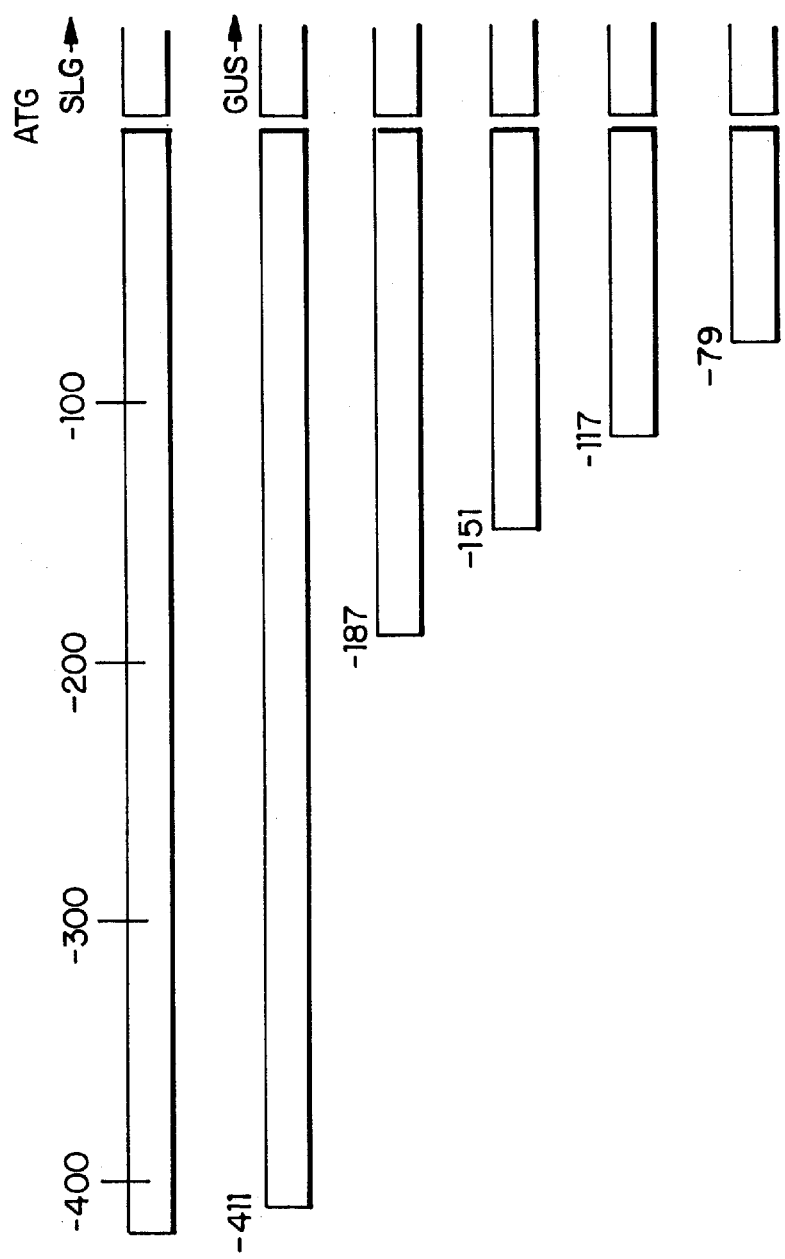
FIG. 1 depicts sequential 5' deletions of the $SLG_{13}$ promoter fused to the β-glucuronidase (GUS) indicator gene. The 5' endpoints of the promoter deletions are shown in relation to the $SLG_{13}$ promoter (top). The deletion endpoints are numbered from the translation initiation codon of the $SLG_{13}$ promoter.

The present invention identifies minimal promoter elements required for the expression of a gene in the pistil or anther. Further, while the invention is described by reference to the S-locus glycoprotein (SLG) gene promoter and the S-locus related (SLR1) gene promoter of Brassica, it is understood that the invention is not limited thereto. Also, while transgenic tobacco plants were used as the experimental system, and while there are minor species-dependent differences in the activity of the SLG promoter, it is understood that tobacco is well suited for the functional dissection of this promoter because the dual activity of the promoter in pistil and pollen is maintained in this easily transformable plant.

To find pistil- and anther-specifying domains of the SLG promoter, several truncated versions of the promoter taken from the $SLG_{13}$ allele were constructed. Sequential 5' deletions of the promoter, or short promoter modules inserted upstream of a minimal promoter derived from the cauliflower mosaic virus (CaMV) 35S promoter (P. N. Benfey, L. Ren and N. H. Chua, EMBO J., Vol. 9, (1990) pages 1677–1684), were used to direct the expression of the GUS reporter gene in transgenic tobacco. The results established that distinct promoter elements direct GUS activity in pistil and pollen. A 196 bp region (-339 to -143) is sufficient to confer pistil-specificity to the marker gene. Two distinct, but functionally redundant, domains (-415 to -291 and -117 to -8) allow expression of the gene in the anther.

As used herein, the term "isolated" with respect to DNA elements, means DNA elements that are not in their natural environment. That is, the DNA elements are not in a full length DNA strand found in nature. The element might have been isolated from the full length DNA strand via experimental techniques, such as use of restriction endonuclease enzymes and cloning or amplification by the polymerase chain reaction. The elements also might have been produced synthetically.

The term "pistil-specific" as used herein means expression confined to cells of the pistil —the stigma, the transmitting tissue of the style and ovary—and exclusive of any other cells in the plant body.

The term "anther-specific" as used herein means confined to cells of the anther—the tapetal cells, developing microspores, and pollen—and exclusive of any other cells in the plant body.

The term "minimal promoter" as used herein means a region from any promoter that provides a TFIID binding site (a TATA box) and a transcription initiation site.

As used herein, the phrase "functional equivalents" in the context of isolated DNA elements means DNA fragments that function the same, qualitatively, as the first mentioned isolated DNA elements. Thus, if the isolated DNA element directs pistil-specific expression of a gene, a DNA fragment would be a functional equivalent if the DNA fragment also directed pistil-specific expression of a gene operably linked to the fragment in the same manner as the isolated DNA element. Quantitative equivalence is not needed for a fragment to be a functional equivalent according to this invention. Thus DNA fragments that have nucleotide substitutions, deletions and/or additions can be functional equivalents of an isolated DNA element.

In order to determine whether a DNA fragment is a "functional equivalent" of an isolated DNA element, the following assay(s) can be conducted. The promoter fragment is linked to a reporter gene such as β-glucuronidase or a toxic gene such as the diphtheria toxin subunit A, and introduced into plants. Promoter activity is analyzed by assays for β-glucuronidase activity or by visual inspection for toxic gene expression. These assays are described in Thorsness et al., Dev. Biol., Vol. 143, (1991) pages 173–184.
Construction of Isolated DNA Element that Directs Pistil- or Anther-Specific Expression The isolated DNA elements of the present invention that direct pistil- or anther-specific expression can be constructed by PCR or by making deletions of suitable promoters, or by synthetic methods. For example, promoter fragments can be generated by PCR utilizing the SLG promoter of the $S_{13}$ SLG allele as a template. The endpoints of these fragments relative to the translation initiation codon are -339 to from -143 to -79 for pistil-specific expression and -415 to -291 or −117 to −8 for pollen-specific expression. Promoter fragments also can be made from promoters of other alleles of the SLG, such as S$_2$' S$_8$ and R1, alleles of SRK, alleles of SLR1, and any other related or unrelated genes with expression patterns similar to SLG and SLR1. Preferably the promoters from which the promoter fragments are obtained contain sequence motifs of the five consensus sequences denoted as SEQ ID NOS:1–5. The endpoints of the promoter fragments can be determined based on sequence comparisons.

As will be more apparent from Example III herein, pistil- and anther-specific DNA elements also can be patterned after parts of the sequences disclosed in FIGS. 3(A) and 3(B) (SEQ ID NOS:6–10), and especially those parts including the sequences found in the Boxes. Consensus sequences have been determined for each Box and are as follows: Box I, GACNAATGATA (SEQ ID NO:1); Box II, GTTTGT (SEQ ID NO:2); Box III, TGANTTAATCG (SEQ ID NO:3); Box IV, TGAAAAAGTCATNGA (SEQ ID NO:4); and Box V, ATTTTNCTTGTCTGCT (SEQ ID NO:5). In the consensus sequences N is A, T, C, G or a deletion.

Thus according to one embodiment of the present invention, the isolated DNA element that directs pistil-specific expression of a gene comprises three sequence motifs that have about 70% or more homology sequence identity to the three consensus sequences denoted as SEQ ID NO:1, SEQ ID NO:2 and SEQ ID NO:3, with greater degrees of homology, e.g., 80%, 90%, 95% or more being more preferred.

According to another embodiment of the present invention, the isolated DNA element that directs anther-specific expression of a gene comprises a sequence motif that has about 60% or more homology to the consensus sequence denoted as SEQ ID NO:5. Again, greater degrees of homology, e.g., 70%, 80%, 90%, 95% or more are preferred.

In an even further embodiment of the present invention, the isolated DNA element that directs anther-specific expression of a gene has about 60% or more, preferably 70%, 80%, 90%, 95% or more, homology to the −415 to −291 region of the sequence set forth in FIG. 3(B) nucleotides 1–186 of SEQ ID NO:6.

Construction of Isolated DNA Element-Promoter Polypeptide or RNA-Encoding Gene Fusions Methods are known in the art for construction of DNA elements operably linked to promoters. (Sambrook et al, "Molecular Cloning, a Laboratory Manual", 2nd ed., Cold Spring Harbor Laboratory Press, N.Y., 1989 Vol. 1–3) Such methods could utilize an intermediate vector which can be any vector suitable for cloning and can be prepared by fusing a promoter, preferably a minimal promoter, to a polypeptide or RNA-encoding gene followed at the 3' end by a polyadenylation and transcription termination region of any plant gene.

Based on the orientation of the isolated DNA element relative to the restriction endonuclease sites of the vector, appropriate strategies can be taken to couple the isolated DNA element to the promoter and polypeptide or RNA-encoding gene.

The polypeptide or RNA-encoding gene can be any DNA sequence encoding a desired polypeptide or RNA. In a preferred embodiment of this invention, a gene that encodes a moiety cytotoxic to plant cells, or alternatively that perturbs pistil function or development, is linked to the female specific DNA element thereby causing female sterility. Similarly a gene that encodes a moiety cytotoxic to plant cells, or that perturbs anther function or development, is linked to the male specific DNA element thereby causing male sterility.

Examples of such genes are listed in European Patent Application Number 90402196.1, publication number 0 412 006 Al, filed Jul. 31, 1990, the disclosure of which is hereby incorporated by reference.

Preferred examples of genes encoding moieties cytotoxic to plant cells include the genes which are described in the following references, the disclosures of which are hereby incorporated by reference:

a) Pectate lyase gene pelE from *Erwinia chrysanthemi* EC16, which degrades pectin, causing cell lysis. Kenn et al., J. Bacteriology, Vol. 168, (1986) page 595.

b) Diphtheria toxin A-chain gene (DTA), which inhibits protein synthesis, Greenfield et al., PNAS, U.S.A., Vol. 80, (1983) page 6853; Palmiter et al., Cell, Vol. 50, (1987) page 435.

c) T-urfl3 (TURF-13) gene from cms-T maize mitochondrial genomes; this gene encodes a polypeptide designated URF13 which disrupts mitochondrial or plasma membranes. Braun et al., Plant Cell, Vol. 2, (1990) page 153; Dewey et al., PNAS, U.S.A., Vol. 84, (1987) page 5374; and Dewey et al., Cell, Vol. 44, (1986) page 439.

d) Gin recombinase gene from phage Mu gene, which encodes a site-specific DNA recombinase which will cause genome rearrangements and loss of cell viability when expressed in cells of plants. Maeser et al., Mol. Gen. Genet., Vol. 230, (1991) pages 170–176. A mutant gene, which is not host dependent, is also disclosed in Maeser et al.

e) Indole acetic acid-lysine synthetase gene (iaaL) from *Pseudomonas svringae*, which encodes an enzyme that conjugates lysine to indoleacetic acid (IAA). When expressed in the cells of plants, it causes altered development due to the removal of IAA from the cell via conjugation. Romano et al., Genes and Development, Vol. 5, (1991) pages 438–446; Spena et al., Mol. Gen. Genet., Vol. 227, (1991) pages 205–212; Robert et al., PNAS, U.S.A., Vol. 87, pages 5795–5801.

f) CytA toxin gene from *Bacillus thuringiensis* Israeliensis which encodes a protein that is mosquitocidal and hemolytic. When expressed in plant cells, it causes death of the cell due to disruption of the cell membrane. McLean et al., J. Bacteriology, Vol. 169, (1987) pages 1017–1023; Ellar et al., U.S. Pat. No. 4,918,006 (1990).

Especially preferred are constructions employing the pelE gene driven by an SLG$_{13}$ promoter fragment that directs pistil-specific expression.

Other genes useful in creating female and male sterility include those encoding Adenine Phosphoribosyltransferase (APRT) (Moffatt and Somerville, Plant Physiol., Vol. 86, (1988) pages 1150–1154); DNase, RNase; proteases and salicylate hydroxylase.

It is further recognized that RNA which is capable of disrupting the formation of viable pollen or the flower, seed or embryo can be utilized in the present invention. The RNA of the invention includes anti-sense RNA as well as ribozymes.

Anti-sense RNA can be utilized which will hybridize with MRNA from a gene which is critical to pollen formation or function, e.g., APRT, or which is critical to flower, seed or embryo formation or function. In this manner, the anti-sense RNA will prevent expression of the necessary genes resulting in no pollen formation or no flower or seed formation, respectively.

Alternately, ribozymes can be utilized which target mRNA from a gene which is critical to pollen, flower, seed, or embryo formation or function. Such ribozymes will comprise a hybridizing region of at least about nine nucleotides which is complementary in nucleotide sequence to at least part of the target RNA and a catalytic region which is adapted to cleave the target RNA. Ribozymes are described in EPA No. 0 412 006, EPA No. 0 321 201 and W088/04300 herein incorporated by reference. See, also Haseloff and Gerlach, Nature, Vol. 334, (1988) pages 585–591; Fedor and Uhlenbeck, Proc. Natl. Acad. Sci., U.S.A., Vol. 87, (1990) pages 1668–1672; Cech and Bass, Ann. Rev. Biochem., Vol. 55, (1986) pages 599–629; T. R. Cech, Vol. 236, (1987) pages 1532–1539; T. R. Cech, Gene, Vol. 73, (1988) pages 259–271; and, Zang and Cech, Science, Vol. 231, (1986) pages 470–475.)

The construct may also include any other necessary regulators such as terminators, (Guerineau et al., Mol. Gen. Genet., Vol. 226, (1991) pages 141–144; Proudfoot, Cell, Vol. 64, (1991) pages 671–674; Sanfacon et al., Genes Dev., Vol. 5, (1991) pages 141–149; Mogen et al., Plant Cell, Vol. 2, (1990) pages 1261–1272; Munroe et al., Gene, Vol. 91, (1990) pages 151–158; Ballas et al., Nucleic Acids Res., Vol. 17, (1989) pages 7891–7903; Joshi et al., Nucleic Acid Res., Vol. 15, (1987) pages 9627–9639); plant translational consensus sequences (C. P. Joshi, Nucleic Acids Research, Vol. 15, (1987) pages 6643–6653), introns (Luehrsen and Walbot, Mol. Gen. Genet., Vol. 225, (1991) pages 81–93) and the like, operably linked to the nucleotide sequence. It may be beneficial to include 5' leader sequences in the expression cassette construct. Such leader sequences can act to enhance translation. Translational leaders are known in the art and include:

Picornavirus leaders, for example, EMCV leader (Encephalomyocarditis 5' noncoding region) (0. Elroy-Stein, T. R. Fuerst and B. Moss, PNAS, U.S.A., Vol. 86, (1989) pages 6126–6130);

Potyvirus leaders, for example, TEV leader (Tobacco Etch Virus) (Allison et al., (1986); MDMV leader (Maize Dwarf Mosaic Virus); Virology, Vol. 154, pages 9–20), and Human immunoglobulin heavy-chain binding protein (BiP), (D. G. Macejak and P. Sarnow, Nature, Vol. 353, (1991) pages 90–94;

Untranslated leader from the coat protein mRNA of alfalfa mosaic virus (AMV RNA 4), (S. A. Jobling and L. Gehrke, Nature, Vol. 325, (1987) pages 622–625;

Tobacco mosaic virus leader (TMV), (D. R. Gallie et al., Molecular Biology of RNA, (1989) pages 237–256; and Maize Chlorotic Mottle Virus leader (MCMV) (S. A. Lommel et al., Virology, Vol. 81, (1991) pages 382–385. See also, Della-Cioppa et al., Plant Physiology, Vol. 84, (1987) pages 965–968.

Signal sequences may be included within the expression cassette of the invention. Such signal sequences may be any DNA sequence which is able to direct the transport of an associated polypeptide. The signal sequence is preferably a sequence which is translated into a signal peptide, which becomes separated from the peptide after transit of the peptide is complete. Signal sequences are useful for directing the polypeptide product of the coding DNA sequence to a desired location within the cell, such as to the mitochondria or to the endoplasmic reticulum, or to direct extracellular transport outside of the cell. Among the signal sequences useful for the present invention are, for example, the signal sequence from the pathogenesis-related gene (PR-1) of tobacco, which is described in Cornellisen et al., EMBO, Vol. 5, (1986) pages 37–40; the yeast mitochondrial presequence; Schmitz et al., Plant Cell, Vol. 1, (1989) pages 783–791; the signal sequence from plant mitochondrial Rieske iron-sulfur protein, Huang et al., PNAS, U.S.A., Vol. 88, (1991) pages 10716–10720; mitochondrial and chloroplast (1989). The identification of other leader sequences is known in the art. See Delle-Cioppa et al., Plant Physiology, Vol. 84, (1987) pages 965–968; Schekman, TIBS, (1985) page 188.

A plant terminator may be utilized in the expression cassette. See, Rosenberg et al., Gene, Vol. 56, (1987) page 125; Guerineau et al., Mol. Gen. Genet., Vol. 226, (1991) pages 141–144; Proudfoot, Cell, Vol. 64, (1991) pages 671–674; Sanfacon et al., Genes Dev., Vol. 5, (1991) pages 141–149; Mogen et al., Plant Cell, Vol. 2, (1990) pages 1261–1272; Munroe et al., Gene, Vol. 91, (1990) pages 151–158; Ballas et al., Nucleic Acids Res., Vol. 17, (1989) pages 7891–7903; Joshi et al., Nucleic Acid Res., Vol. 15, (1987) pages 9627–9639.

Plant Transformation

The aforementioned isolated DNA element-promoter-polypeptide or RNA-encoding-gene fusions can be introduced into an appropriate vector for transforming plants, e.g., agrobacteria, and the resulting bacterial strains can be used to transform plants to achieve a variety of effects, including female or male sterility.

Methodologies for the construction of plant expression cassettes as well as the introduction of foreign DNA into plants is generally described in the art. Generally, for the introduction of foreign DNA into plants Ti plasmid vectors have been utilized for the delivery of foreign DNA as well as direct DNA uptake, liposomes, electroporation, microinjection, and the use of microprojectiles. Such methods have been published. See, for example, Guerche et al., Plant Science, Vol. 52, (1987) pages 111–116; Neuhause et al., Theor. Appl. Genet., Vol. 75, (1987) pages 30–36; Klein et al., Nature, Vol. 327, (1987) pages 70–73; Howell et al., Science, Vol. 208, (1980) page 1265; Horsch et al., Science, Vol. 227, (1985) pages 1229–1231; DeBlock et al., Plant Physiology, Vol. 91, (1989) pages 694–701; Methods for Plant Molecular Biology, (Weissbach and Weissbach, eds.) Academic Press, Inc. (1988); and Methods in Plant Molecular Biology, (Schuler and Zielinski, eds.) Academic Press, Inc. (1989). It is understood that the method of transformation will depend upon the plant cell to be transformed.

It is further recognized that the components of the expression cassette may be modified to increase expression. For example, truncated sequences, nucleotide substitutions or other modifications may be employed.

As mentioned above, a preferred embodiment of the present invention is to use the isolated DNA elements to direct the expression of a gene that will kill or otherwise interfere with the function of pistil cells or anther cells. The pistil is the female reproductive structure of the plant, the function of which is to support germination and growth of the pollen tube until it reaches the ovule and can fertilize the egg cell. Interference with this function thus renders the plant female sterile. The ability to control the female fertility of plants is useful in the production of hybrid seed. The production of female sterile plants is described in European Patent Application number 90402196.1, Publication Number 0 412 006 Al filed Jul. 31, 1990, the disclosure of which is hereby incorporated by reference.

Briefly, the method of EP 0 412 006 Al involves transforming a plant with a foreign DNA sequence which encodes a product which selectively disrupts the metabolism, functioning and/or development of cells of the flowers. Pages 5–6 of the application list female-sterility DNAs any of which would be useful in the present invention.

Male sterile plants according to the present invention can be made by known methods analogous to those described for making female sterile plants. Male sterile plants are useful in breeding schemes for producing commercially desirable hybrids.

Plantlets resulting from independent transformation events can be propagated and analyzed. The presence of inserted DNA sequences in the putative transgenic plants can be verified by DNA blot analysis or PCR as described in the examples herein.

EXAMPLES

The invention will now be described by reference to specific examples, which are not meant to be limiting.

In the following examples nucleotide position numbering of the $SLG_{13}$ promoter follows that set forth in FIGS. 3(A) (SEQ ID NOS:6–9) and 3(B) nucleotides 1–186 of SEQ ID NO:6.

EXAMPLE I

CONSTRUCTION OF PROMOTER FRAGMENTS

Construction of 5' Promoter Deletions

The starting point for the construction of sequential 5' deletions of the $SLG_{13}$ promoter was an $SLG_{13}$ promoter-GUS-nos gene fusion consisting of a 3.65 kb promoter fragment fused to the β-glucuronidase reporter gene and to the polyadenylation signal and transcription termination region of the nopaline synthase (nos) gene of Agrobacterium tumefaciens (M. K. Thorsness, M. K. Kandasamy, M. E. Nasrallah and J. B. Nasrallah, Dev. Biol., Vol. 143, (1991) pages 173–184). The promoter fragment in this gene fusion extends from a natural BamH1 site 3.65 kb 5' of the $SLG_{13}$ protein-coding region to a BamH1 site that was introduced by site-directed mutagenesis at nucleotide –8 (8 bp upstream of the ATG initiating codon) in the $SLG_{13}$ gene (M. K. Thorsness, M. K. Kandasamy, M. E. Nasrallah and J. B. Nasrallah, Dev. Biol., Vol. 143, (1991) pages 173–184). This $SLG_{13}$-GUS-nos fusion was cloned into the Bluescript (Stratagene) plasmid to generate plasmid pJSS1. pJSS1 was used to generate a deletion derivative to a natural HpaI site found in the $SLG_{13}$ promoter at nucleotide –411. The resulting plasmid, pMKT29, was in turn used to generate two additional deletion derivatives: one in which sequences were deleted to the ClaI site at –151, and another in which sequences were deleted to the DraI site at –79.

Additional 5' promoter deletions were generated by the polymerase chain reaction (PCR) with pMKT29 as template. Deletions were directed to positions –187 and to –117 in the $SLG_{13}$ promoter by using, as 5' amplimers, synthetic oligonucleotides complementary to sequences at these positions, and as 3' amplimer an oligonucleotide complementary to a sequence located within the β-glucuronidase coding region. The BamH1 site (at position –8 from the ATG) in the PCR-amplified fragments was used to insert the promoter fragments upstream of GUS-nos. The correct orientation and sequence of the fusions was verified by DNA sequence analysis. The endpoints of these derivatives (numbered from the translation initiation codon) and their respective orientations are given in FIG. 1. Each of these promoter constructs retains the putative TATA-binding site found in the SLG promoter. A polyadenylation site is included at the terminus of the GUS coding region. The gene fusions were cloned into the binary vector pBIN19 (M. Bevan, Nucleic Acids Res., Vol. 12, (1984) pages 8711–8721).

Construction of Promoter Fragment-Minimal Promoter-GUS Fusions

Figure 2:
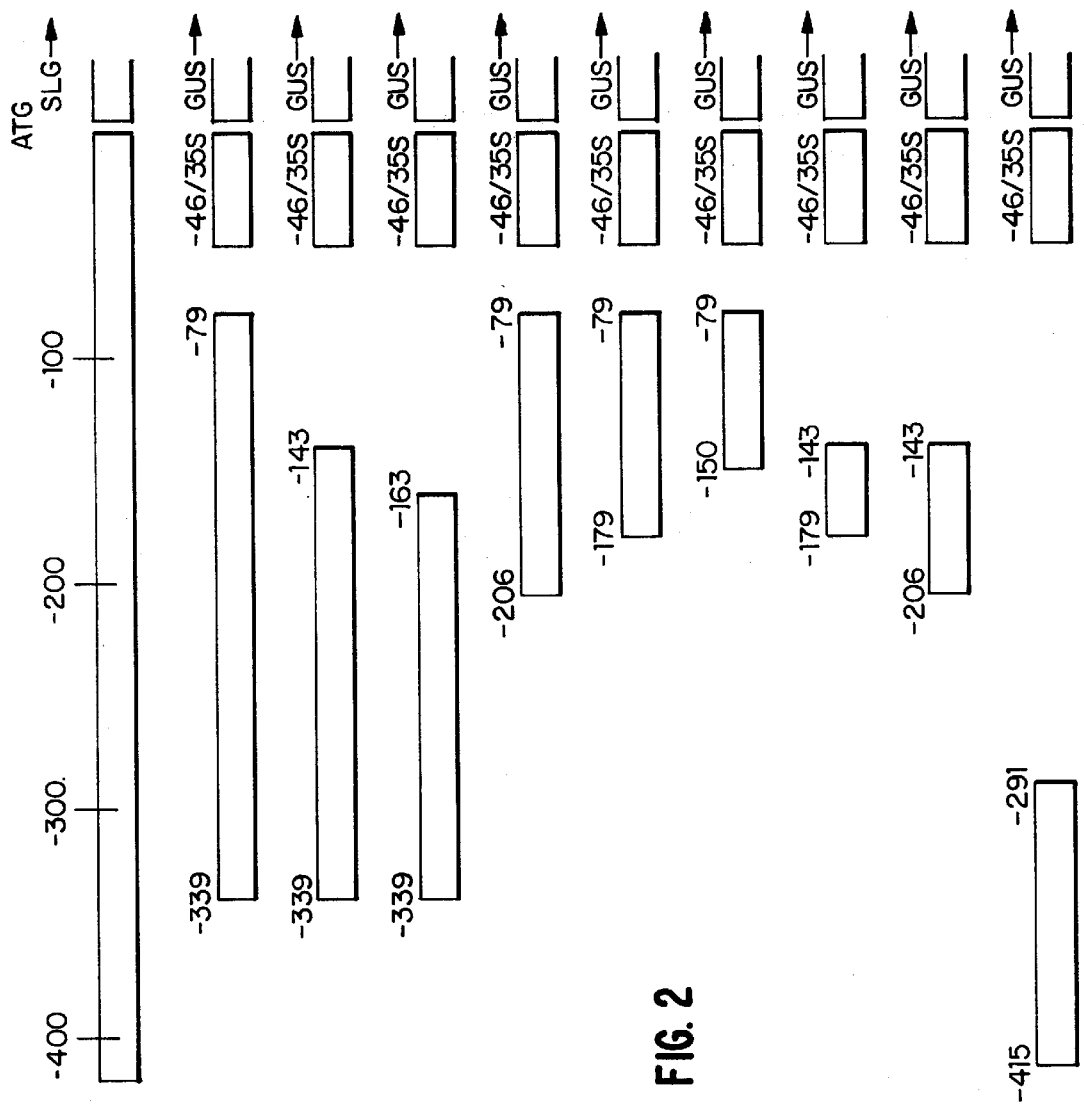
FIG. 2 depicts PCR-generated promoter modules derived from the $SLG_{13}$ promoter. The promoter modules were joined to the "TATA box" region of the CaMV 35S (-46/35S) promoter and to β-glucuronidase. The 5' and 3' endpoints of the promoter modules are shown in relation to the $SLG_{13}$ promoter (top).
Figure 5:
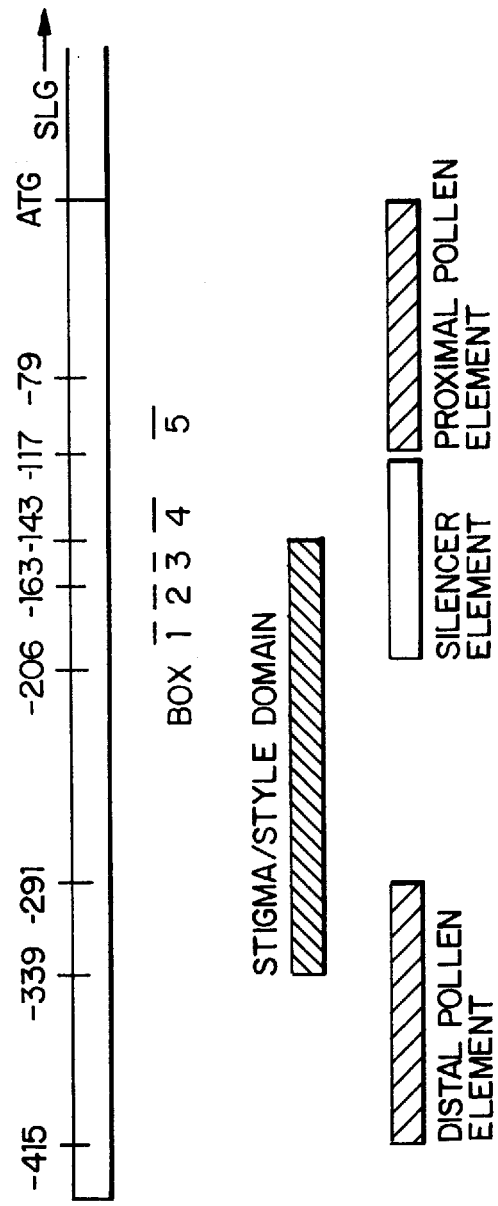

Individual promoter modules were synthesized from the 5' upstream region of the $SLG_{13}$ allele by PCR and joined to the –46 to +8 region of the CaMV 35S promoter. This 35S promoter fragment provides the TFIID binding (TATA box) and transcription initiation sites, and has been used as a minimal promoter in studies of plant gene activity (P. N. Benfey, L. Ren and N. H. Chua, EMBO J., Vol. 9, (1990) pages 1677–1684). The endpoints of these fragments relative to the translation initiation codon are shown in FIG. 2. The PCR-amplified products were cloned in the linearized plasmid vector pCR1000 (Invitrogen) and sequenced. Based on the orientation of the promoter fragments relative to the restriction endonuclease sites of the vector, one of two strategies was taken to couple the SLG promoter domain to the minimal promoter and β-glucuronidase.

Plasmids that contained inserts facing "left" (i.e., towards the SpeI site of pCR1000) were opened at the SpeI site and joined to the intermediate vector pEMBL-(GUS-46)-BS at a corresponding SpeI site. In the resulting plasmid, the SLG promoter fragment is linked to the CaMV 35S minimal promoter-GUS fusion. The region of interest was excised from the plasmids as an EcoR1 fragment and cloned into the corresponding site of pBIN19.

The intermediate vector pEMBL-(GUS-46)-BS contained the –46 to +8 region of the CaMV 35S promoter joined to the coding region of the β-glucuronidase gene followed by the polyadenylation and transcription termination region of the ribulose-bis-phosphate carboxylase small subunit (rbcS) gene. This plasmid was generated by cloning a BglII-EcoR1 fragment of pEMBL-(GUS-46), containing the CaMV 35S minimal promoter-GUS-rbcS terminator fusion, into the BamHI-EcoR1 sites of the Bluescript vector.

Plasmids that contained PCR-amplified products facing "right" were opened at a SacI site and fused at this site with pEMBL-(GUS-46)-BS. The resulting plasmids were digested with NotI and relegated to place the promoter fragments adjacent to the CaMV 35S-GUS-rbcS fusion. These constructs were opened at an EcoR1 site and fused at the corresponding site to pBIN19.

EXAMPLE II

PLANT TRANSFORMATION

Plant Transformation

The aforementioned promoter-GUS fusions were introduced into Agrobacterium tumefaciens strain pCIB542/A136 (as one example of a vector for transforming plants). The pCIB542/A136 strain is derived from pEHA101 (E. E. Hood, G. L. Helmer, R. T. Fraley and M.-D. Chilton, J. Bacteriol., Vol. 168, (1986) pages 1291–1301) and the resulting bacterial strains were used to transform axenic excised leaf tissue of N. tabacum cv. Petit Havana as described (R. B. Horsch, J. Fry, N. Hoffman, J. Neidermeyer, S. G. Rogers and R. T. Fraley, In "Plant Molecular Biology Manual", S. B. Gelvin and R. A. Schilperoort, eds., Kluwer Academic Publishers, Dordrecht (1988) pages A5:1–9). Kanamycin-resistant plantlets resulting from independent transformation events were propagated and analyzed. The presence of inserted DNA sequences in the putative transgenic plants were verified in representative numbers of plants for each of the constructs by DNA blot analysis.

Histochemical Analysis

GUS activity was detected using the chromogenic substrate 5-bromo-4-chloro-3-indoyl-β-D-glucuronide (x-gluc) as described (R. A. Jefferson, T. A. Kavanagh and M. W. Bevan, EMBO J., Vol. 6, (1987) pages 3901–3907). Pistil sections that included the stigma and style were dissected longitudinally and incubated at 37° C. in 2 mM x-gluc, 0.1M NaPO4 (pH 7.0), 0.5% (v/v) Triton X-100 for 16 to 18 hrs. The tissue was destained in increasing concentrations of ethanol to a final concentration of 95% (v/v) ethanol and observed under a dissecting microscope. Due to oxidative discoloration of the tissue surface, some of the samples were further dissected. Pollen grains were taken from several anthers of an open flower by tapping the grains into the well of a microtiter plate. Pollen was incubated in the above assay buffer at 37° C. for 4 to 8 hrs., rinsed in 50% (v/v) ethanol, and viewed under a dissecting microscope. Sections of leaf, steam, root, petal, sepal, anther and filament tissue were analyzed as per pistil sections. Representative pollen and pistil sections were photographed under a phase contrast and dissecting microscope, respectively.

The results of this analysis are summarized in Table 1 below.

TABLE 1

Histochemical Localization of GUS Activity Conferred by SLG 5' Promoter Deletions and SLG-promoter Fragment-35S-GUS Fusions.

| Construct Endpoints | TATA Element | Pistil Expression | Pollen Expression |
|---|---|---|---|
| −411 | SLG | 5/7 | 5/7 |
| −187 | SLG | 0/18 | 0/18 |
| −187R | SLG | 0/10 | 0/10 |
| −151 | SLG | 0/20 | 0/20 |
| −117 | SLG | 0/18 | 13/18 |
| −79 | SLG | 0/5 | 0/5 |
| −339 to −79 | 35S | 20/24 | 0/24 |
| −339 to −143 | 35S | 10/21 | 0/21 |
| −339 to −163 | 35S | 0/17 | 0/17 |
| −206 to −79 | 35S | 0/17 | 0/17 |
| −179 to −79 | 35S | 0/7 | 0/7 |
| −150 to −79 | 35S | 0/20 | 0/20 |
| −179 to −143 | 35S | 0/22 | 0/22 |
| −206 to −143 | 35S | 0/16 | 0/16 |
| −415 to −291 | 35S | 0/10 | 9/10 |
| (none) | 35S | 0/6 | 0/6 |
| wild type | — | 0/4 | 0/4 |

Endpoints of promoter fragments are given in the first column. The TATA element used in a particular construction is indicated in the second column: SLG = native SLG TATA element; 35S = −46 to +8 CaMV 35S minimal promoter. The number of plants exhibiting GUS activity following staining with x-gluc is given over the number of independently isolated transgenic plants analyzed. "R" = reverse orientation.

Pistil-Specific Expression

A photograph of a longitudinal section through the upper region of a tobacco pistil showed that at the apex of the pistil was a bilobed stigma consisting of a papillate epidermis, a subepidermal zone, and parenchymatous ground tissue. The secretory zone of the stigma converged into the style as a central region of transmitting tissue surrounded by the cortex and the epidermis. During pollination, pollen germinates at the stigma surface, and the pollen tubes extend into the transmitting tissue of the style as they make their way towards the ovary. Untransformed tobacco pistils do not contain detectable endogenous GUS activity, and did not stain with x-gluc.

Tobacco plants transformed with three of the $SLG_{13}$ promoter constructs exhibited GUS activity in the stigma and style (Table 1). From the first set of sequential 5' promoter deletions, only one of the fragments, that having an endpoint at −411, directed GUS expression in the pistil. Activity was apparent along the length of the transmitting tissue of the style, in the stigma, and in papillar cells. GUS activity was detected in these tissues in each of the flower bud stages examined, ranging from buds 1.2cm in length to open flowers. No activity was detected in leaf, root, anther, petal, sepal, or stem. The pattern of expression observed with the −411 construct was similar to that seen when a 3.65 kb SLG promoter-GUS fusion is introduced into Nicotiana (M. K. Thorsness, M. K. Kandasamy, M. E. Nasrallah and J. B. Nasrallah, Dev. Biol., Vol. 143, (1991) pages 173–184).

These data suggested that the DNA elements required for pistil-specific expression are located downstream of the −411 endpoint. The pistil-specifying ability of fragments with endpoints within this region was assayed in the second set of constructions. Of the fragments joined to the minimal promoter and GUS, two tested positive for GUS activity. A region spanning from −339 to −79 and a 196 bp fragment with endpoints at −339 and −143 gave results that were very similar to the −411 construct described above. Expression was detected in the stigma secretory zone, stylar transmitting tissue, and in stigma papillar cells. However, the intensity of expression from the shorter (−339 to −143) fragment was noticeably less than that from the −411 and the −339 to −79 constructs. In addition, fewer of these transformed plants stained positive for GUS activity: blue staining was noted in 5 of 7 plants transformed with the −411 fragment and in 20 of 24 plants transformed with the −339 to −79 fragment, but in only 10 of 21 plants transformed with the shorter fragment (Table 1). GUS activity was detected in pistils of open flowers and in buds as small as 1.6cm in length and was not detected in other floral or vegetative tissues. Narrowing the 3' end of the 196 bp fragment by only 20 bp to −163 or decreasing the 5' end to −206 leads to the loss of GUS expression (Table 1). Plants transformed with a construct containing the −46 to +8 CaMV 35S minimal promoter region linked alone to GUS or with a 5' deletion having the −187 fragment in reverse orientation (−187R) did not show GUS activity in pistils (Table 1).

Pollen-Specific Expression

Three of the constructs allow for consistent GUS expression in pollen (Table 1). Of the sequential promoter deletions, both the −411 and −117 constructs showed activity in pollen, while constructs with endpoints in between did not have activity (Table 1). Of the 35S minimal promoter fusions, one construct, with endpoints of −415 and −291, exhibited GUS activity in pollen. Other than the −411 deletion, none of these constructs conferred expression in the pistil. Conversely, the 196 bp pistil-specific domain and the pistil- specifying −339 to −79 35S-GUS fusion did not exhibit consistent pollen expression (Table 1). On occasion, light-blue staining was noted for pollen of plants containing other constructs; however, this staining was not evident in further screenings of these plants.

For each of the pollen expressing constructs, expression was noted only in pollen of open flowers and was not seen in pollen from flowers of earlier stages of development. Staining was limited to pollen and was not detected in the sporophytic tissue of the anther. In some of the plants, approximately one half of the pollen grains showed GUS activity, consistent with the introduction of a single copy of the gene into the genome of these plants. For several of the plants, expression in pollen varied, and may, perhaps, be influenced by an unknown environmental factor. Staining was not observed in pollen of untransformed plants or in pollen of plants transformed with the 35S minimal promoter fused alone to GUS (Table 1).

EXAMPLE III

DETERMINATION OF THE NUCLEOTIDE SEQUENCE OF SLG AND SLR1 PROMOTER REGIONS

The isolation of SLG alleles was previously described: $SLG_{13}$ was isolated from a B. oleracea cv. acephala (kale)

S13 homozygote (J. B. Nasrallah, S. M. Yu and M. E. Nasrallah, Proc. Natl. Acad. Sci., U.S.A., Vol. 85, (1988) pages 5551–5555); $SLG_2$ from a *B. oleracea cv. alboglabra* $S_2$ homozygote (C. H. Chen and J. B. Nasrallah, Mol. Gen. Genet., Vol. 127, (1990) pages 221–228); $SLG_8$ from the *B. campestris* $S_8$ homozygote (K. Toriyama, J. C. Stein, M. E. Nasrallah and J. B. Nasrallah, Theor. Appl. Genet., Vol. 81, (1991) pages 769–776). The SLR1 gene was isolated from a *B. oleracea cv. acephala* $S_{22}$ homozygote as follows. Genomic DNA was prepared from leaf tissue, purified on CsCl gradients, digested with EcoR1, and fractionated on agarose gels. The region of the gel that contained the SLR1 gene, previously identified by DNA gel blot analysis, was excised from the gel. The DNA was eluted and used to construct a sub-genomic library in the bacteriophase λGEM11 (Stratagene). SLR1-containing clones were identified by hybridization to an SLR1-cDNA probe (B. A. Lalonde, M. E. Nasrallah, K. G. Dwyer, C. H. Chen, B. Barlow and J. B. Nasrallah, Plant Cell, Vol. 1, (1989) pages 249–258).

For nucleotide sequence analysis, restriction fragments containing sequences 5' of the initiating ATG codon were subcloned into appropriate plasmid vectors. For the $SLG_{13}$ and $SLG_2$ genes, restriction fragments were subcloned into the M13 vectors mp18 and mp19 (C. Yanisch-Perron, J. Vieira and J. Messing, Gene, Vol. 33, (1985) pages 103–119) and single-stranded DNA templates were sequenced by the dideoxynucleotide chain termination method (F. Sanger, S. Nicklen and A. R. Coulson, Proc. Natl. Acad. Sci., U.S.A., Vol. 74, (1977) pages 5463–5467). For the $SLG_8$ and SLR1 genes, restriction fragments were subcloned into the pUC118 and pUC119 vectors (J. Vieira and J. Messing, Methods Enzymol., Vol. 153, (1987) pages 3–11). A series of nested deletions were generated by ExoIII digestion using the Erase-A-Base kit (Promega), and the DNA sequence was determined on double-stranded plasmid templates (E. Y. Chen and P. H. Seeburg, DNA, Vol. 4, (1985) pages 165–170).

The nucleotide sequences of the promoter regions of 3 alleles of the Brassica SLG gene—$SLG_{13}$ and $SLG_2$ from *B. oleracea*, and $SLG_8$ of *B. campestris*—and one allele of the SLR1 gene were determined. The S-locus related gene, SLR1, is a member of the S-gene family that is unlinked to the S-locus, and is expressed in a manner similar to SLG (B. A. Lalonde, M. E. Nasrallah, K. G. Dwyer, C. H. Chen, B. Barlow and J. B. Nasrallah, Plant Cell, Vol. 1, (1989) pages 249–258; M. Trick and R. B. Flavell, Mol. Gen. Genet., Vol. 218, (1989) pages 112–117; R. M. Hackett, M. J. Lawrence and F. C. H. Franklin, Plant J., Vol. 2, (1992), pages 613–617). The four promoter regions share a high degree of sequence homology with five elements being particularly conserved. These five boxes are shown aligned in FIG. 3(A) (SEQ ID NOS:6–9) and Boxes I to V have the consensus sequences denoted as: SEQ ID NO:1; SEQ ID NO:2; SEQ ID NO:3; SEQ ID NO:4; and SEQ ID NO:5, respectively. Within each box, actual sequence homology is about 70% for Box I, about 80% for Box II, about 80% for Box III, about 50% for Box IV and about 60% for Box V. In addition, several stretches of sequence similarity are found between individual genes. For example, the $SLG_{13}$ and $SLG_8$ alleles are 85% identical over 202 bp, while the $SLG_2$ allele is only 66% identical to $SLG_{13}$ over 289 bp. The $SLR_1$ sequence is the least conserved and shares approximately 40% sequence identity with the $SLG_2$ and $SLG_{13}$ alleles.

FIG. 4 is a diagram showing the arrangement of the functional elements within the $SLG_{13}$ promoter.

While the invention has been described in detail and with reference to specific embodiments thereof, it will be apparent to one skilled in the art that various changes and modifications can be made therein without departing from the spirit and scope thereof.

What is claimed is:

1. An isolated DNA element that directs expression of an operably linked coding sequence of a gene comprising a sequence selected from the −339 to −79 region or the −339 to −143 region of the SLG$_{13}$ promoter
    wherein said DNA element is linked to a minimal promoter.

2. A chimeric gene comprising a DNA element comprising SEQ ID NO:1, SEQ ID NO:2 and SEQ ID NO:3 operably linked to a coding sequence of at least one gene that encodes a polypeptide or RNA,
    wherein said coding sequence does not naturally occur in operable linkage with said DNA element, and
    said DNA element directs pistil-specific expression of said coding sequence in either a 5' or 3' or a 3' to 5' orientation with respect to the coding sequence, wherein said DNA element is linked to a mimimal promoter.

3. A transgenic plant having integrated into its genome the chimeric gene of claim 2.

4. The transgenic plant of claim 3, wherein said gene encodes a polypeptide or RNA that is cytotoxic.

5. The transgenic plant of claim 4, wherein said gene comprises a gene selected from the group consisting of the pectate lyase gene pelE from *Erwinia chrysanthemi* EC16, the Diphtheria toxin A-chain gene, the T-urf 13 gene from cms-T maize mitochondrial genomes, the gin recombinase gene from phage Mu gene, the indole acetic acid-lysine synthetase gene from *Pseudomonus syringae*, and the CytA toxin gene from *Bacillus thuringiensis* Israeliensis.

6. The transgenic plant of claim 5, wherein said gene comprises the pectate lyase gene PelE from *Erwinia chrysanthemi* EC16.

7. The transgenic plant of claim 3, wherein said gene encodes at least one protein selected from the group consisting of adenine phosphoribosyltransferase, DNase, RNase, protease and salicylate hydroxylase.

8. The transgenic plant of claim 4, wherein said gene encodes a ribozyme.

9. The transgenic plant of claim 4, wherein said gene encodes an anti-sense RNA.

10. The DNA element of claim 1, wherein said gene encodes a ribozyme or an anti-sense RNA.

11. The DNA element of claim 1, wherein said minimal promoter is Cauliflower mosaic virus (CAMV) 35S promoter.

12. A chimeric gene comprising a DNA element of the SLG13 promoter from the −339 to −79 region or from −339 to −143 region operably linked to a coding sequence of a gene that encodes a polypeptide or RNA, wherein said coding sequence does not naturally occur in operable linkage with said DNA element, and said DNA element directs pistil-specific expression of said coding sequence in either a 5' or 3' or a 3' to 5' orientation with respect to the coding sequence.

13. The DNA element of claim 12, wherein said minimal promoter is Cauliflower Mosaic Virus (CAMV) 35S promoter.

14. The DNA element of claim 12, wherein said minimal promoter is SLG13 promoter.

15. A transgenic plant having integrated into its genome the chimeric gene of claim 12.

16. The transgenic plant of claim 15, wherein said gene encodes a polypeptide or RNA that is cytotoxic.

17. The transgenic plant of claim 15, wherein said gene comprises a gene selected from the group consisting of the pectate lyase gene PelE from *Erwinia chrysanthemi* EC16, the Diphtheria toxin A-chain gene, the T-urf 13 gene from cms-T maize mitochondrial genomes, the gin recombinase gene from phage Mu gen, the indole acetic acid-lysine synthetase gene from *Psuedomous syringae*, and the CytA toxin gene from *Bacillus thuringiensis* Israeliensis.

18. The transgenic plant of claim 16, wherein said gene encodes at least one protein selected from the group consisting of adenine phosphoriboxyltransferase, DNase, RNase, protease and salicylate hydroxylase.

19. The transgenic plant of claim 15, wherein said gene encodes a ribozyme.

20. The transgenic plant of claim 15, wherein said gene encodes an anti-sense RNA.

21. A method of selectively expressing at least one gene that encodes a polypeptide or RNA in a plant pistil, said method comprising growing a transgenic plant having integrated into its genome the chimeric gene claims 12.

* * * * *

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
        ( A ) LENGTH: 11 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:1:

G A C N A A T G A T A                                                                                                 1 1

( 2 ) INFORMATION FOR SEQ ID NO:2:

( i ) SEQUENCE CHARACTERISTICS:
        ( A ) LENGTH: 6 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:2:

GTTTGT 6

(2) INFORMATION FOR SEQ ID NO:3:

(i) SEQUENCE CHARACTERISTICS:
        (A) LENGTH: 11 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:3:

TGANTTAATCG 11

(2) INFORMATION FOR SEQ ID NO:4:

(i) SEQUENCE CHARACTERISTICS:
        (A) LENGTH: 15 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:4:

TGAAAAAGTC ATNGA 15

(2) INFORMATION FOR SEQ ID NO:5:

(i) SEQUENCE CHARACTERISTICS:
        (A) LENGTH: 16 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:5:

ATTTTNCTTG TCTGCT 16

(2) INFORMATION FOR SEQ ID NO:6:

(i) SEQUENCE CHARACTERISTICS:
        (A) LENGTH: 475 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

```
TGCTGAGATG GATTTACAAT TTGATTTCTT TTGTATTTTT ATTGGTGTG TTTAATATAT    60
TAGTTAACCA ATTTACGTTA TACCAAATTT TTCAACCCTC TTTTTAGTAA AAAACGAAAT   120
TAAAGTTTTT TCCCTCTTAG TCCGACGATT TTAAGCTAAT TAGTTCGAAC AAAGAGTACA   180
ACATTAATTT TCTAACAGAC TTAGATGCAC TTGCGAACAA CATACTTGCT GAACACCATA   240
TGTTATGTTG GCAGGGTGAG AAATTAATCA CGTGTAGATA TAGAAGTAGT AGACAAATGA   300
TATAGGTTTG TGGGAATGAA TTAATCGATG GGATGAAAAA GTCATCGAAC ATGTAACACC   360
ACATTTTACT TGTCTGCTAG GTTCGTGATA GTCGTTTAAA TTAGATACGT GAAAAAAGAT   420
TATAAATATG CAAAAGGGGA AGGGAAGAA AAGAAAGAAA AAGGAGGGGA GAGAA         475
```

(2) INFORMATION FOR SEQ ID NO:7:

(i) SEQUENCE CHARACTERISTICS:
    (A) LENGTH: 311 base pairs
    (B) TYPE: nucleic acid
    (C) STRANDEDNESS: double
    (D) TOPOLOGY: linear (ii) MOLECULE TYPE: DNA (genomic)

(xi) SEQUENCE DESCRIPTION: SEQ ID NO:7:

| | | | | | | |
|---|---|---|---|---|---|---|
| ACTTGAATGT | ATCGAATCAT | ACTATTGAGA | CCACCATACT | TGCGGAATAC | CATATGCTAT | 60 |
| GTTGACAGCG | TGAGAACTAA | TAACGTGTAG | ATATAAAAGT | AGTTGACTGA | ATGATACAAG | 120 |
| TTTGTGGAAG | TGACTTAATC | GTAGGGATGA | AAAAGTCATG | GACTATGGAA | CACAACATTT | 180 |
| TGCTTGCCAG | TTAGGTTCGT | CATAATAGTT | TAATTCGAAT | TTTCTTGCAA | AGTAACTTAG | 240 |
| GATGTATATA | TATGTGCAAG | TAGGACAAAA | ACTAACAACA | AGAAAAAAAA | AGAAAGAAAG | 300 |
| TGGTGGGGAA | A | | | | | 311 |

(2) INFORMATION FOR SEQ ID NO:8:

(i) SEQUENCE CHARACTERISTICS:
    (A) LENGTH: 202 base pairs
    (B) TYPE: nucleic acid
    (C) STRANDEDNESS: double
    (D) TOPOLOGY: linear (ii) MOLECULE TYPE: DNA (genomic)

(xi) SEQUENCE DESCRIPTION: SEQ ID NO:8:

| | | | | | | |
|---|---|---|---|---|---|---|
| GTAGTAGGTA | TAAAAGTAGT | GGACAAATGA | TACACGTTTT | TGGAAATGAA | TTAATCGATG | 60 |
| GGATGAAAAA | GTCATCGAAC | ATGTAACACC | ACATTTTGCT | TGTCTGCTAG | GTTCCTTATA | 120 |
| GTCGTTTAAA | ATCTGTATGT | GGAAAAGATT | ATAAATAAGC | AAGGGGAGGG | GGAAAGAAAG | 180 |
| AAAGAACAAG | GTGGGGAGAG | AA | | | | 202 |

(2) INFORMATION FOR SEQ ID NO:9:

(i) SEQUENCE CHARACTERISTICS:
    (A) LENGTH: 356 base pairs
    (B) TYPE: nucleic acid
    (C) STRANDEDNESS: double
    (D) TOPOLOGY: linear (ii) MOLECULE TYPE: DNA (genomic)

(xi) SEQUENCE DESCRIPTION: SEQ ID NO:9:

| | | | | | | |
|---|---|---|---|---|---|---|
| TTTTAAGTCA | AACTGAAGGA | AACAACATAT | GATATGTTAT | GTCATTTGGT | CCAAAAACAC | 60 |
| AATGTTACGT | TGCATGAGAA | ATCAATTTCA | CGTGGTAAGG | TTACTGACCA | ATGACAATAG | 120 |
| TTTGTTAAAA | TGAGTTAATG | AGTGGCTGGA | AAGTCATAGA | ATGTGGAAAT | AAAAAATTTT | 180 |
| CTTGTCTGCT | GGAAAGTATA | TAATATCTAC | AATTAAGACA | TAAACCATGC | AAATTAAAAT | 240 |
| CAAACCATCC | TCATTAGGTT | TGCAAATCTA | ATAAAGACAT | AAAGTCCATA | TGTAACAATT | 300 |
| TTTTTCTATA | AATAACGGGC | GACAATGCAT | AGAAAATTAA | AGTGGTGAAG | AGAGAG | 356 |